US008801776B2

(12) United States Patent
House et al.

(10) Patent No.: US 8,801,776 B2
(45) Date of Patent: Aug. 12, 2014

(54) INFUNDIBULAR REDUCER DEVICES

(75) Inventors: Morgan House, Newfields, NH (US);
Philipp Bonhoeffer, London (GB);
Nasser Rafiee, Andover, MA (US);
Rany Huynh Busold, Charlestown, MA (US); Nareak Douk, Lowell, MA (US);
Juan-Pablo Mas, Indianapolis, IN (US);
Stuart MacDonald, Haverhill, MA (US); Michael Finney, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 316 days.

(21) Appl. No.: 12/391,330

(22) Filed: Feb. 24, 2009

(65) Prior Publication Data

US 2010/0049306 A1     Feb. 25, 2010

Related U.S. Application Data

(60) Provisional application No. 61/031,266, filed on Feb. 25, 2008.

(51) Int. Cl.
*A61F 2/06*          (2013.01)

(52) U.S. Cl.
USPC ........... 623/1.26; 623/1.15; 623/1.2; 623/1.3; 623/1.31

(58) Field of Classification Search
CPC ...................................... A61F 2/07; A61F 2/06
USPC ..................... 623/1.13, 1.15, 1.18, 1.23, 1.24
See application file for complete search history.

(56) References Cited

U.S. PATENT DOCUMENTS

| 5,480,424 | A | 1/1996 | Cox |
| 6,293,968 | B1* | 9/2001 | Taheri .......................... 623/1.15 |
| 6,719,789 | B2 | 4/2004 | Cox |
| 7,413,573 | B2* | 8/2008 | Hartley et al. ............... 623/1.13 |
| 2002/0138135 | A1 | 9/2002 | Duerig et al. |
| 2003/0149477 | A1* | 8/2003 | Gabbay ........................ 623/2.14 |
| 2003/0199963 | A1 | 10/2003 | Tower et al. |

(Continued)

FOREIGN PATENT DOCUMENTS

| WO | WO2004/096100 | 11/2004 |
| WO | WO2005/096993 | 10/2005 |
| WO | WO2006/127412 | 11/2006 |
| WO | WO2007/071436 | 6/2007 |

OTHER PUBLICATIONS

Bonheoffer et al., "Percutaneous Insertion of the Pulmonary Valve" Journal of the American College of Cardiology 2002; 39: 1664-1669.

(Continued)

*Primary Examiner* — David Isabella
*Assistant Examiner* — Yashita Sharma (57) ABSTRACT

Described is a prosthetic valve assembly comprising: a radially self-expandable stent configured to expand to bear against a wall of a native body lumen; and an implantable prosthetic valve, having a diameter, the valve being mounted inside the stent; wherein the diameter of the stent is greater than the diameter of the prosthetic valve.

22 Claims, 7 Drawing Sheets

(56) References Cited

U.S. PATENT DOCUMENTS

| | | |
|---|---|---|
| 2003/0199971 A1 | 10/2003 | Tower et al. |
| 2004/0210307 A1 | 10/2004 | Khairkhahan |
| 2004/0260389 A1* | 12/2004 | Case et al. .................. 623/1.24 |
| 2005/0085894 A1 | 4/2005 | Kershner |
| 2005/0182483 A1* | 8/2005 | Osborne et al. ............. 623/1.24 |
| 2006/0052867 A1 | 3/2006 | Revuelta et al. |
| 2007/0244546 A1 | 10/2007 | Francis |
| 2008/0208314 A1* | 8/2008 | Skerven ....................... 623/1.15 |

OTHER PUBLICATIONS

Bonheoffer et al., "Transcatheter Replacement of a Bovine Valve in Pulmonary Position" Circulation 2000; 102:813-816.

Khambadkone et al., "Percutaneous Pulmonary Valve Implantation in Humans" Circulation, 1189-1197, Aug. 3, 2005.

* cited by examiner

INFUNDIBULAR REDUCER DEVICES

CROSS-REFERENCE TO RELATED APPLICATION

The present application claims priority to U.S. Provisional Application No. 61/031,266, filed Feb. 25, 2008, and titled "Infundibular Reducer and Related Devices," the entire contents of which is incorporated herein by reference in its entirety.

TECHNICAL FIELD

This invention relates generally to the treatment of cardiac valve disease using prosthetic valves, and more particularly to replacement of malfunctioning pulmonary valves using infundibular reducer devices.

BACKGROUND OF THE INVENTION

Natural heart valves, such as aortic valves, mitral valves, pulmonary valves and tricuspid valves, often become damaged by disease in such a manner that they fail to maintain blood flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement generally has been accomplished by major open heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, co-existing infection, or other physical limitations.

Recently, there has been increasing interest in minimally invasive and percutaneous replacement of cardiac valves, typically by way of catheterization. In minimally invasive procedures, a catheter is used to insert a mechanical or bioprosthetic valve in a lumen of a blood vessel via percutaneous entry through a distal blood vessel. Typically, such percutaneous prosthetic valve devices comprise an expandable stent segment, a stent anchoring segment and a flow-regulation segment, such as a ball valve or a biological valve. The expandable stent portion is generally expanded using a balloon that is part of a transcatheter delivery system.

In the specific context of pulmonary valve replacement, U.S. Patent Application Publication Nos. 2003/0199971 A1 and 2003/0199963 A1, both filed by Tower, et al. and incorporated herein by reference, describe replacing a pulmonary valve with a venous valvular replacement. The replacement pulmonary valve is mounted on a balloon catheter and delivered percutaneously via the vascular system to the location of the failed pulmonary valve and expanded by the balloon to compress the native valve leaflets against the right ventricular outflow tract, anchoring and sealing the replacement valve. As described in the articles: *Percutaneous Insertion of the Pulmonary Valve*, Bonhoeffer, et al., Journal of the American College of Cardiology 2002; 39: 1664-1669 and *Transcatheter Replacement of a Bovine Valve in Pulmonary Position*, Bonhoeffer, et al., Circulation 2000; 102: 813-816, both incorporated herein by reference in their entireties, the replacement pulmonary valve may be implanted to replace native pulmonary valves or prosthetic pulmonary valves located in valved conduits. Surgical procedures for percutaneous pulmonary valve implantation are described in Khambadkone et al., *Percutaneous Pulmonary Valve Implantation in Humans*, Circulation, 1189-1197 (Aug. 23, 2005).

Pulmonary valve replacement using venous valves is not available to all who might benefit from it due to the relatively narrow size range of available valved segments of veins, for example, with typical sizes available only up to a diameter of about 22 mm.

Unfortunately, many patients requiring pulmonary valve replacement are adults and children who have right ventricular outflow tracts that are larger than 22 mm in diameter. This could have resulted, for example, from having previously undergone transannular patch repair of tetralogy of Fallot during infancy. There are other causes, however, for an enlarged right ventricular outflow tract. Thus, venous valvular replacements, having an upper limit of 22 mm on their diameters, cannot typically be securely implanted within these patients.

Thus, there is a continuing need to improve upon the devices available for heart valve replacement, in particular those including venous valve replacements and pericardial valve replacements, and even more particularly those that may be placed in patients with irregular right ventricular outflow tracts (e.g., right ventricular outflow tracts that are larger than 22 mm in diameter, or irregular in shape).

SUMMARY OF THE INVENTION

The present invention provides infundibular reducer devices used for replacing a malfunctioning heart valve, and in particular, a pulmonary heart valve. The infundibular reducer devices may be delivered through percutaneous transcatheter implantation to an anatomic site within or near the heart. The devices are at least partially self-expandable, and have modularity, such that segments of the devices are independently expandable with respect to other segments of the devices. Preferably, the infundibular reducer devices include a pericardial heart valve or a valved segment of bovine jugular vein, for example, and are implanted in the right ventricular outflow tract, for example. In addition, however, it is contemplated that the present inventive devices may include other collapsible valves and may be implanted in other anatomical sites in the body.

A benefit of some embodiments of the present invention is that the devices may be delivered through a catheter to a desired anatomic site and may expand without a need for a balloon to expand the devices. Delivery of devices without a balloon minimizes the bulkiness of the delivery system, which can allow for easier insertion and removal of the devices.

Another benefit of the present invention is that modularity of the devices allows different segments of the devices to expand and move independently. Thus, the devices are able to conform more closely to an irregular implanted site. Certain segments of the devices may rotate with respect to other segments, and the devices may shorten and lengthen. The devices are also able to move within the implanted site during the cardiac cycle, and still conform to the implanted site. As a result, the devices are more effective.

Another benefit of the devices is that the devices may be collapsed and repositioned after partial deployment or partial expansion. This is beneficial if it is determined during early stages of delivery of one of the devices that the device is not being placed correctly. The device may then be re-compressed and moved to a correct location.

Yet another benefit of the devise of the present invention is that the devices are easily explantable. The stent portion may be peeled from the wall of the implanted site, collapsed, and the valve and stent may then be removed from the body.

A further benefit of the present invention is that drastic failure of the devices due to fracture of one wire or a few wires is eliminated. Since the stent portions of the devices are comprised of a plurality of wires that are independently connected in a plurality of locations to the fabric frame, fracture of one wire or a few wires does not cause the whole device to fail.

A still further benefit of some embodiments of the invention is that the devices may include features that allow the devices to be located using fluoroscopy, for example. Fluoroscopy may be helpful in placement of the devices as well as for later identification purposes.

An additional benefit of some embodiments of the devices is that the devices may include materials that are antimicrobial, prevent thrombosis, and either increase or reduce tissue ingrowth. Such materials allow the devices to be better secured in a vessel, and decrease the chance of rejection of the devices.

Another benefit of the present invention is that the stent portion may later serve as a landing zone or site for implantation of a later-needed prosthetic valve. Another valve may be delivered percutaneously to the inner lumen of the device that is already implanted.

A first aspect of the present invention is a prosthetic valve assembly. One embodiment comprises: a radially self-expandable stent configured to expand to bear against a wall of a native body lumen; and an implantable prosthetic valve, having a diameter, the valve being mounted inside the stent; wherein the diameter of the stent is greater than the diameter of the prosthetic valve. The stent may comprise a plurality of wires. The plurality of wires may comprise a material having shape memory, or the plurality of wires may comprise a plurality of different materials. The plurality of wires may be circular in shape and include a plurality of sinusoidal bends. The sinusoidal bends in the wires may have different sizes. At least some of the plurality of wires are in a nested configuration. At least some of the plurality of wires are in a point-to-point configuration. The stent may comprise a middle portion having a smaller diameter than at end portions thereof, and the valve may be mounted in the middle portion. The stent may comprise a middle portion having a diameter and end portions thereof may have tapered diameters in directions toward the middle portion, and the valve may be mounted in the middle portion. The middle portion may be cylindrical in shape. The stent may comprise a plurality of wires attached to at least one piece of fabric. The middle portion and each end portion articulate with respect to each other.

A second embodiment of the invention is a prosthetic valve assembly comprising: a radially self-expandable stent comprising a middle portion having a smaller diameter than end portions thereof, with the end portions configured to expand to bear against a wall of a native body lumen; and an implantable prosthetic valve mounted inside the middle portion of the stent. The stent may comprise a plurality of wires. The plurality of wires may comprise a plurality of different materials. The plurality of wires may be circular in shape and include a plurality of bends. The bends in the wires may be sinusoidal in shape. The plurality of wires may comprise a material having shape memory. The end portions may have tapered diameters in directions toward the middle portion. The middle portion may be cylindrical in shape. The stent may comprise a plurality of wires attached to at least one piece of fabric. The middle portion and each end portion articulate with respect to each other. At least some of the plurality of wires are in a nested configuration. At least some of the plurality of wires are in a point-to-point configuration.

A third embodiment of the present invention is a prosthetic valve assembly comprising: a radially self-expandable stent configured to expand to bear against a wall of a native body lumen, the stent comprising: a plurality of wires; and at least one piece of fabric to which the plurality of wires are attached; and an implantable prosthetic valve mounted inside the stent; wherein the plurality of wires of the stent are individually expandable and compressible providing the assembly with modularity. The plurality of wires comprise circular wires having a plurality of bends around the circumference of the circular wires. The plurality of wires may be in a nested configuration or a point-to-point configuration or a combination thereof. The plurality of wires may comprise a material having shape memory.

BRIEF DESCRIPTION OF THE DRAWINGS

The present invention will be further explained with reference to the appended Figures, wherein like structure is referred to by like numerals throughout the several views, and wherein.

DETAILED DESCRIPTION

With reference to the accompanying figures, wherein like components are labeled with like numerals throughout the figures, illustrative infundibular reducer and related devices are disclosed, taught and suggested by the multiple embodiments. Although the devices are called "infundibular reducer" devices, the devices may be used in anatomic locations other than the infundibulum, such as the right ventricular outflow tract and other locations in or near the heart. In particular, the devices allow for prosthetic heart valves to be implanted in the right ventricular outflow tract or the infundibulum. The purpose of such devices is to allow replacement valves, such as pericardial heart valves, for example, having a smaller diameter than the diameter of the implanted site (e.g., the right ventricular outflow tract) to be implanted. However, the devices generally disclosed and shown may be used for other purposes as well.

The devices disclosed are beneficially configured such that the devices fit well in irregularly-shaped anatomy. The infundibular reducer devices of the present invention are preferably at least partially self-expandable. In addition, the devices are modular, which means that different segments of the devices are somewhat independent in their ability to expand and move. Thus, the devices are able to conform more closely to an irregularly shaped implant site. In addition, the modularity of the devices allows different segments of the devices to move with respect to one another in order to accommodate the movement of different segments of the implant site during a cardiac cycle, for example. The feature of the devices that allows for the modularity is the plurality of wires that comprise the device. These wires are preferably independently connected to one piece of fabric, for example. The configuration of and the material that comprises each of the plurality of wires may vary in order to provide additional modularity of the devices. As a result of the modularity, in particular, some segments of the devices may expand to greater diameters than other segments. Segments may rotate with respect to other segments. Also, the devices may be able to shorten and lengthen. Thus, the modularity also allows the devices to better fit in an irregularly shaped implant site and move within the site during a cardiac cycle, for example. Thus, the devices are more stable in the implant site, and are more effective. The better contact that the device has with the wall of the implant site, the more stable the device is in the site, which prevents paravalvular leaks around the device.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

Figure 1:
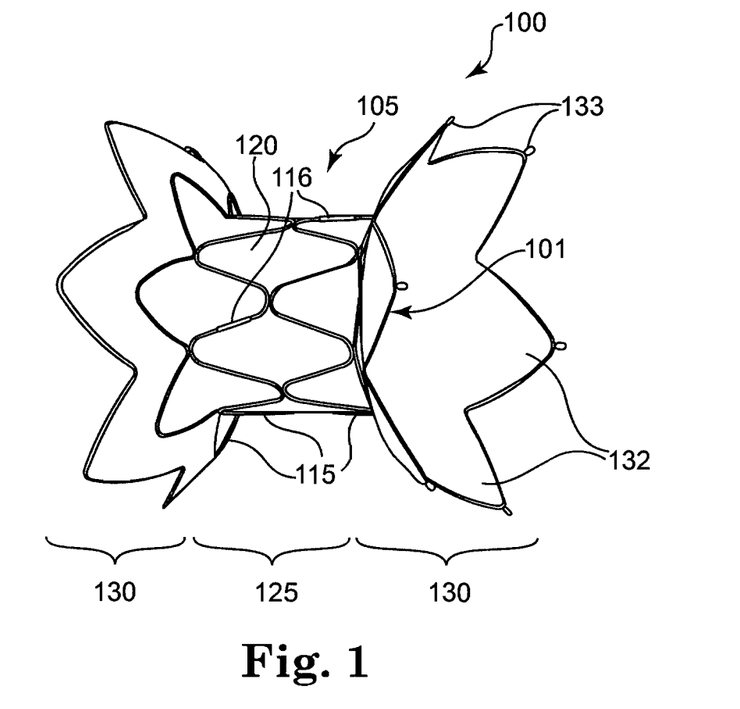
FIG. 1 is a perspective view of an infundibular reducer device, in accordance with the present invention.
Figure 2:
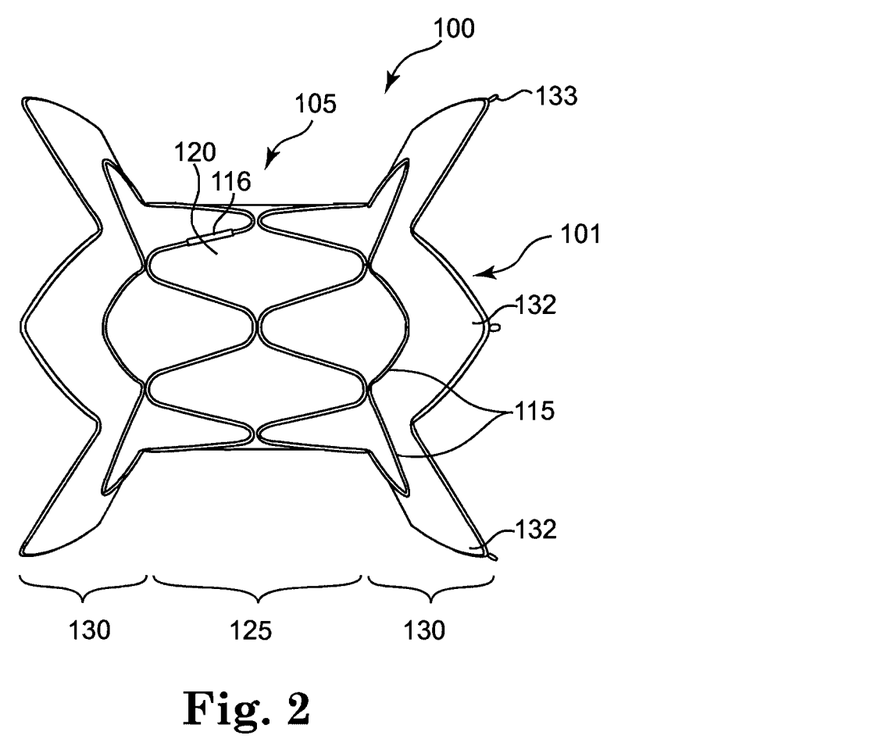
FIG. 2 is a side view of the infundibular reducer device of FIG. 1.
Figure 3:
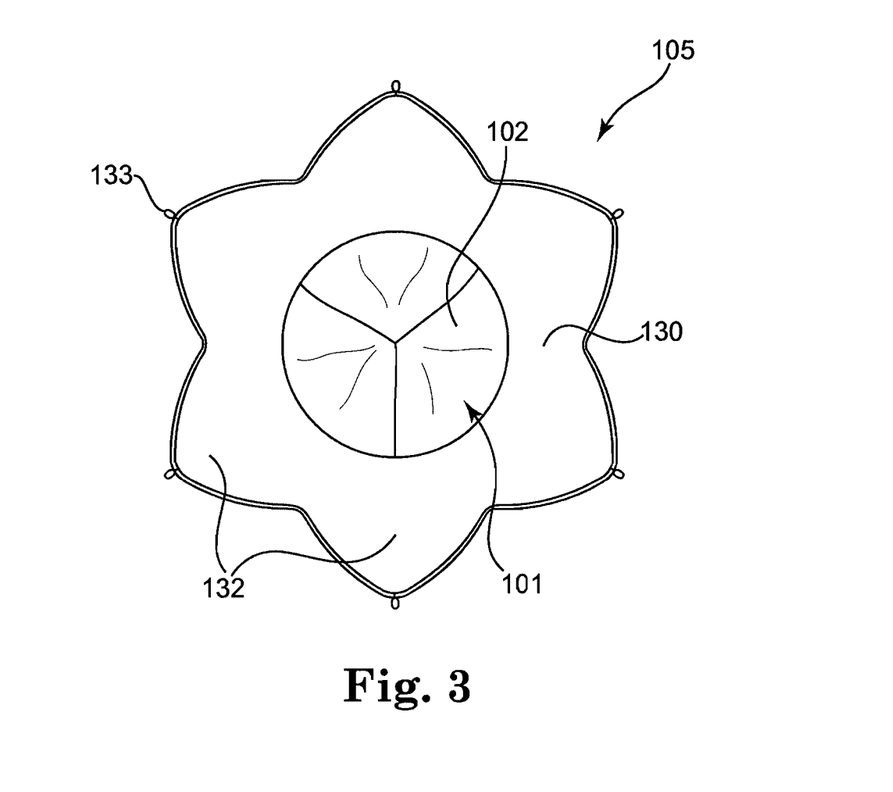
FIG. 3 is an end view of the infundibular device of FIGS. 1 and 2.

Referring now to FIGS. 1-3, an infundibular reducer device 100, in accordance with the present invention, is shown. The infundibular reducer device 100 comprises a self-expandable stent portion 105 and a replacement valve portion 102 (visible in FIG. 3).

The infundibular reducer device 100 is preferably compressible to be inserted via catheter and expandable to fit a desired body lumen, such as the infundibulum or the right ventricular outflow tract. The device 100 is preferably self-expandable from a first reduced diameter to a second enlarged diameter. The device 100 is also preferably modular in expandability, meaning that different segments of the device 100 may independently expand from a first reduced diameter to a second enlarged diameter, and such different segments may rotate with respect to each other and/or cause the device 100 to shorten and lengthen. Such modularity of expandability of the device 100 allows the device 100 to fit in an irregularly shaped implantation site (e.g., the right ventricular outflow tract).

In order to be self-expandable and modular, the stent 105 is preferably formed from a plurality of wires 115 that are shaped in order for the stent portion 105 (and specifically different segments of the stent 105) to have a desired expanded configuration. The plurality of wires 115 should allow the stent portion 105 to be compressed to a particular shape and size, and also allows the stent to regain the desired expanded configuration upon release from compression. The wires 115 preferably include a series of sinusoidal bends around their circumference, as shown in FIGS. 1-3, which allow for the compression and expansion of the stent 105 with minimal force. The shapes of the wires 115 may include sinusoidal bends that resemble a sine wave with rounded apices, or the wires 115 have a zig-zag design that resembles more of a triangular wave form and with sharper apices having a smaller interior angle. The angles of the wires 115 may depend upon the diameter of the wires 115 and the material comprising the wires 115. Other shapes of the wires 115, beside those shown, having, for example, different shapes, angles and numbers of apices, are also contemplated by the present invention.

Each of the plurality of wires 115 is preferably circular in shape, without free ends. However, other shapes are contemplated. The ends of each of the plurality of wires 115 are preferably joined using a crimped hypotube 116, as shown in FIG. 1, that surrounds the ends and joins them. However, it is contemplated that the ends of the wires 115 may be joined using any other possible means for attachment (e.g., gluing or melting ends of wires 115 together).

The wires 115 preferably include sinusoidal bends around their circumference. Each of the sinusoidal bends (or other shapes, as discussed above) of the wires 115 includes an apex, and as shown, the apices of each wire 115 may each contact an apex of an adjacent wire 115 (i.e., a point-to-point configuration). Alternatively, the sinusoidal bends may line up, follow, or "nest" together and will not contact each other at apices (i.e., a nesting configuration). It is also contemplated, however, that adjacent wires within a single device may have different numbers of sinusoidal bends and apices, and therefore, less than all of the apices of adjacent wires may have either a point-to-point configuration or a nesting configuration, and it is possible to have a combination of both configurations in one device. The different configurations of the wires 115, such as the point-to-point configuration and the nesting configuration may result in different load distribution to the anatomy at the implanted site. For example, separate joints will distribute the load more than those that are connected, such as in a point-to-point configuration. The different configurations of the wires 115 may also allow different movement of the device. For example, if a sufficient amount of the wires 125 are in a nesting configuration, the device may be able to shorten and lengthen.

Preferably, the plurality of wires 115 comprise a material or materials that have shape memory characteristics, such as a nickel-titanium alloy (Nitinol™), or other similar inert biocompatible metal or combination of metals. In one embodiment, the material from which the stents are made includes approximately 54.5 percent to 57 percent nickel, and a majority of the balance of the material comprises titanium, as such percentages are known in the field of medical devices and surgical implants (see ASTM designation: F 2063-00, for example). In the prosthetic valve 100 shown, the stent portion 105 is preferably formed into a desired shape and made from a framework that comprises a plurality of wires 115 made of Nitinol™.

It is possible for device 100 to include a plurality of wires 115, with different wires 115 comprising different materials. In particular, the different materials may have different strengths and may contribute to modularity of the device. For example, different strengths of the wires 115 may result in some wires 115 expanding to a larger or a smaller diameter than other wires 115. For example, one embodiment may include a more stiff or rigid wire material for the wires surrounding the valve portion of the device, in order to stabilize the valve. Meanwhile, the end portions of the device may include wires made of a more flexible material, in order for the end portions to conform more closely to the anatomy of the implantation site.

The plurality of wires 115 of device 100 may also have different configurations. For example, the wires 115 may have different numbers of sinusoidal bends or the amplitudes of such bends may differ. The varying configurations of the wires 115 also contributes to the modularity of the device 100. For example, wires 115 with sinusoidal bends that have a smaller amplitude may be stiffer than those with bends having larger amplitudes. Thus, the configuration of the wires 115, as well as the number of wires 115, and the material comprising the wires 115 may all be varied in order to contribute to a desired modularity of device 100 for a given application.

The wires 115 of the stent portion 105 are preferably shaped, configured and aligned such that a central lumen 101 runs through the center of the stent 105 along its length. Such a central lumen 101 accommodates a replacement valve portion 102 (FIG. 3), such as a bovine jugular vein, a pericardial heart valve, or other collapsible valve, for example. Other biological or prosthetic valves may also be used in the stent portion 105, having a size and shape that accommodates the patient's anatomy. Although only FIG. 3 illustrates the inclusion of the replacement valve portion 102, it is contemplated that any of the devices shown or described herein preferably includes such a replacement valve portion 102.

Preferably, the wires 115 of the invention are formed in their desired circular shape and also preferably including their desired sinusoidal wave pattern. This method of manufacture is preferred because if wires fracture they generally return to their earlier configuration. Thus, if a wire is formed in a flat configuration, it will generally return to that flat configuration. The straightening of a wire in a device may result in failure of the device. Therefore, an advantage of embodiments of the invention is that because the wire 115 are preferably formed in their shaped configurations, if fracture of one wire does occur, the fracture will not result in failure of the device as a whole.

The stent portion 105 of the device 100, of the construction and configuration as herein described, preferably has extremely good flexibility, dimensional stability, very smooth surfaces, a low profile when collapsed and an immunity to fatigue and corrosion. The length of the stent portion 105 can be adjusted or designed by varying the number of wires 115 that are utilized, by varying the arrangement of wires 115, and/or by varying other features of the wires 115 and arrangement of wires 115 as discussed above. The working range of the stent 105 between its collapsed condition/configuration and its expanded condition/configuration can also be adjusted by choosing or designing a certain number of curves, zig-zags or bends in each wire 115. In this way, a stent may be tailored for insertion into a particular body site to provide for the most effective implantation of the replacement valve 102 that is attached to the stent 105.

The shape of the self-expandable stent 105, as shown in FIG. 2 is one exemplary shape, which can be described as a generally hourglass shape. Such an hourglass shape (which is achieved when the stent 105 is in an expanded or partially-expanded configuration) includes a middle portion 125 that is generally cylindrical in shape. This middle portion 125 has a diameter that is preferably at least slightly smaller than the diameter of end portions 130. One advantage of the middle portion 125 having a smaller diameter than the end portions 130 is to allow at least a portion of the middle portion 125 of the stent 105 to hold or retain a replacement valve portion (not visible) (e.g., a valved segment of bovine jugular vein) in its central lumen, when such a replacement valve portion 102 has a smaller diameter than the lumen in which the prosthetic valve 100 is to be placed. The larger diameter of the end portions 130 allows the prosthetic valve 100 to be secured in place in such a tubular organ, or a valved anatomic site, having a diameter larger than that of the replacement valve but smaller than the diameter of the end portions 130. The end portions 130 are also shown to be flared, such that they increase in diameter from where the end portions 130 extend from the middle portion 125. The angle at which these flared end portions 130 extend from the middle portion 125 can vary depending on the desired maximum diameter and desired length of the stent 105, along with other factors.

It is also possible to vary the number, configuration and material of the wires 115 in the middle portion 125 in order to allow the stent 105 to be more rigid in that area, for example. Increased rigidity in the middle portion 125 may assist in better retaining and supporting a replacement valve 102 in the device 100.

The areas of the ends portions 130 that result from bends in the wire 115 on the outer edge of the end portions 130 are referred to as crowns 132 of the device 100. The number, spacing, and amplitude of the crowns 132 can vary the modularity and also the stability of the device 100 in an implanted site. The more spaced out the crowns 132 are, for example, the more flexible are the end portions 130 of the device 100. The invention contemplates many different configurations, numbers and spacings of the crowns 132.

The crowns 132 on at least one of the end portions 130 preferably comprise attachment loops 133. The purpose of the attachment loops 133 is to attach the device 100 to a delivery system. The loops 133 preferably do not impede blood flow through the device 100, and may be located such that the loops 133 are attached to or formed on the outer surface of the crowns 132. The attachment loops 133 may preferably resemble belt loops, however, other shapes are contemplated. The attachment lops 133 may be made from the same material as fabric 120, or the loops 133 may comprise suture material, for example. Other materials for the attachment loops 133 are also contemplated by the present invention, however.

In particular, the attachment loops 13 are threaded onto another component (e.g., a wire in a circular shape with free ends) of the delivery system, which allows the end portion 132 of the device 100 to be compressed and attached to the delivery system. Such a compressed configuration preferably allows the device 100 to be inserted percutaneously. Alternatively, both end portions 130 may include the attachment loops 133 on crowns 132. One example of a delivery system that the device 100 may be attached to by using such attachment lops 133 is described in co-pending patent application Ser. No. 12/358,388 filed on Jan. 23, 2009, titled "Infundibular Reducer Device Delivery System and Related Methods."

In the device 100 shown in the Figures, the end portions 130 can be particularly articulable with respect to the middle portion 125 when the wires 115 used for the framework of the middle portion 125 and end portions 130 are not attached to each other. For example, the end portions 130 may be able to rotate with respect to one another and/or with respect to the middle portion 125. However, it would also be possible for the wires 115 of the middle portion 125 to be attached to the wires 115 of one or both end portions 130, thereby limiting movement.

The replacement valve 102 preferably included in device 100 is a pericardial heart valve or a preserved bovine jugular vein of the type described in the above-cited Bonhoeffer, et al. and Tower, et al. references. Other vessels or donor species may, however, alternatively be employed. Preferably, any collapsible valve may be used.

Such replacement valves 102 (example seen in FIG. 3) may be formed from a variety of materials including biological materials and polymers. Exemplary biological materials include homograft, allograft or xenograft, with xenograft being common and well accepted and usually from bovine, ovine, swine or porcine pericardium, or a combination thereof. For example, polymers include expanded TEFLON™ polymers, high density polyethylene, polyurethane, and combinations thereof. Some examples of replacement valves 102 used in the present invention are described in U.S. Pat. Nos. 6,719,789 and 5,480,424, issued to Cox (which are incorporated herein by reference).

The replacement valve portion 102 is attached to (i.e., affixed to, held by, retained by, etc.) the central lumen of the stent portion 105, and is sutured or otherwise attached within the stent 105. The valve portion 102 may be sutured to the wires 115 and/or the fabric 120 of the stent 105. Other means and method for attaching the replacement valve portion 102 to the stent portion 105 are also contemplated, however. As discussed above, the replacement valve portion 102 is preferably positioned within the middle portion 125 of the device and in the central lumen 101.

Also, in FIG. 1, the stent portion 105 includes one piece of fabric 120 (i.e., cloth, material, etc.) to which the wires 115 are attached or through which the wires 115 are woven. The fabric 120 used for the stent can be a polyester knit, for example, or may instead be an ultra high molecular weight polyethylene (UHMWPE), cotton, or the like. The fabric 120 should be biocompatible and may include a number of different fabrics in different areas of the stent and/or in layers, if desired. It is also contemplated that the device 100 may include more than one piece of fabric 120.

The fabric portion 120 of the present invention provides connection and support for the individual wires 115. The wires 115 are attached to the fabric portion 120, and may be woven through the material or otherwise attached. A benefit to attaching the wires 115 to the fabric 120, and with such regularity (e.g., every 1 to 2 mm along the wires 115), is that if a single wire fails or fractures, the whole device 100 is not rendered defective or a failure. The wires 115 preferably hold open the fabric portion 120. The movement of each wire 115 is independent in the fabric 120 and also limited by the flexibility of the wire 115 itself and by the fabric to some extent. The fabric 120 may comprise stretchable material, such as a knit for example. Alternatively, the fabric 120 may be a non-stretchable woven material, which would restrict the movement of the wires 115 more than a knit material, for example. Thus, the movement of the wires 115 is dependent upon the choice of fabric 120 material as well as the material choice and shape of the wires 115 themselves.

The configuration of the plurality of wires 115 also affects the flexibility and movement of the stent 105. For example, the wires 115 may be nested, as in the embodiment in FIGS. 1-3, or aligned point-to-point, as in the embodiment shown in FIG. 4 (discussed below). The nested configuration allows for more flexibility of the stent 105 than the point-to-point configuration. The nested configuration may also allow the device 100 to be shortened and lengthened. The amount of bends in the wires 115, creating the points, can also affect the flexibility and motion of the wires 115 of the stent 105. This nested configuration of the wires 115 also aids in the retractability of the device 100 and the stability of the device 100 longitudinally.

A point-to-point configuration, in which the apices may be connected together, for example by sutures, may decrease the flexibility of the device 100. Therefore, in order to have a device 100 flexible enough to apply to the right ventricular outflow tract, which is quite irregular, it may be desired to include more nesting of wires 115 than point-to-point connections. Flexibility of the device 100 may be, for example, preferred in order to allow the device 100 to better follow the variations in the right ventricular outflow tract that occur throughout the cardiac cycle. Such flexibility in the device 100 would allow for shortening and lengthening of the device 100 without straining the device 100 throughout the cardiac cycle. However, it is contemplated that for different applications, different amounts of flexibility may be desired. The devices, therefore, may be configured with any combination of wire types, materials and configurations, in order to provide the desired amount of flexibility.

Figure 4:
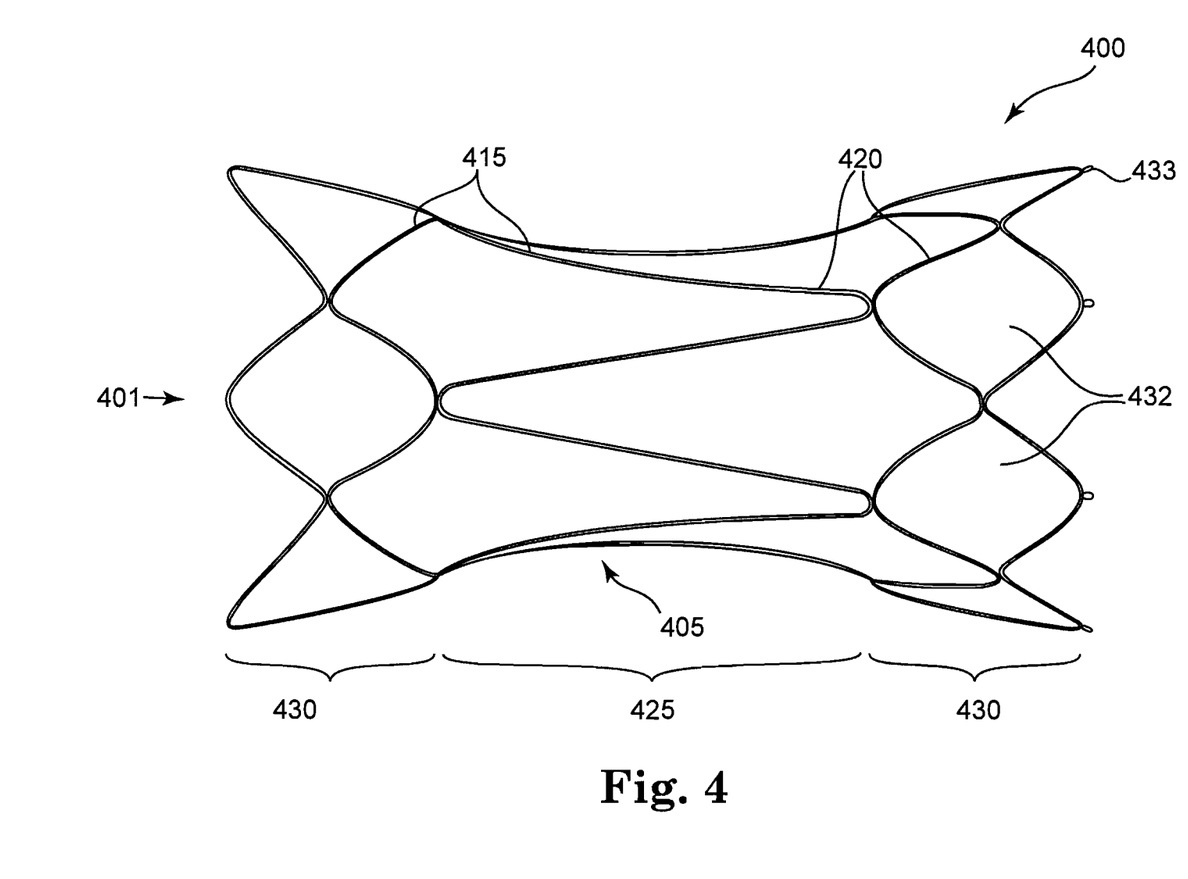
FIG. 4 is a side view of an infundibular reducer device, in accordance with the present invention.

FIG. 4 shows another embodiment of the present invention. Infundibular reducer device 400 is shown and includes a valve portion (not visible) and a stent portion 405 that comprises a plurality of wires 415 and fabric 420. The shape and configuration of device 400 is different from that of device 100 (FIGS. 1-3), including a different number, shape, and arrangement of wires 415. The discussion above with regard to the components of device 100, however, also applies to the corresponding components of device 400. For example, device 400 also includes a middle portion 425 with a generally cylindrical shape and flared end portions 430 that include a generally angled portion and a generally straight portion that forms a cylinder with a diameter that is larger than that of the middle portion 425.

Figure 5:
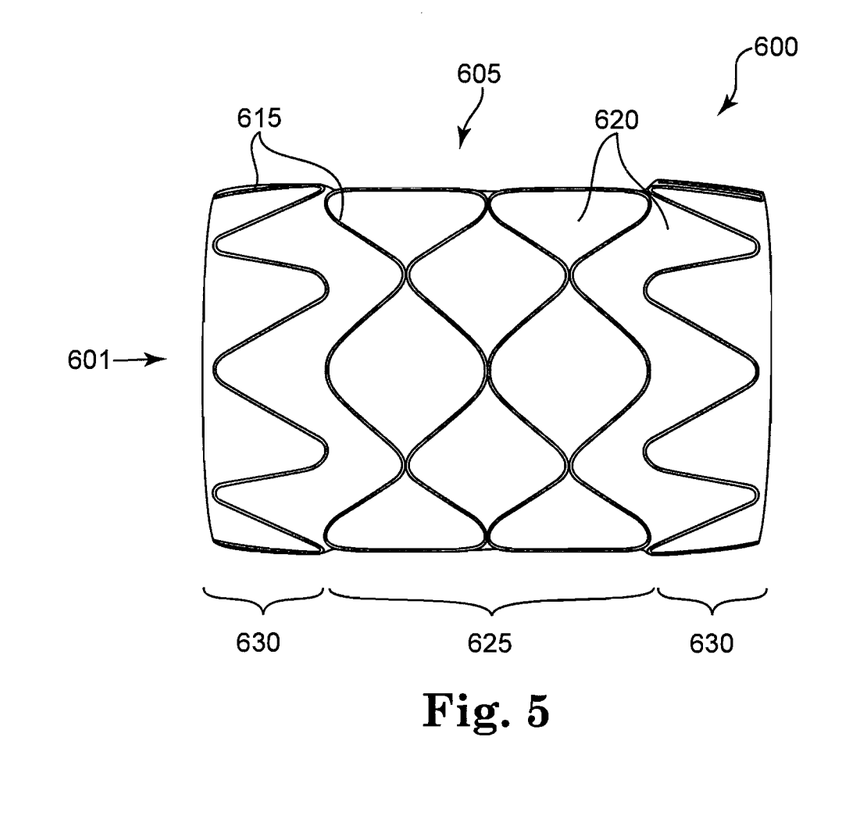
FIG. 5 is a side view of an infundibular reducer device, in accordance with the present invention.

FIG. 5 shows another exemplary infundibular reducer device 600 of the present invention. Again, the shape and configuration of a stent portion 605 is different from that of the stent portions 105, 405 of the earlier described embodiments, including a different number, shape and arrangement of wires 615. However, the description above of the corresponding components of the other stent portions is also applicable to the components of stent 605. Stent 605, however, does not include end portions 630 that have a diameter that is greater than that of the middle portion 625. In this embodiment, the inner lumen (not visible) may be configured such that a valve having a smaller diameter than device 600 may be secured in the inner lumen. The embodiment in FIG. 5 illustrates one of a plurality of configurations that are contemplated by the present invention.

Figure 6:
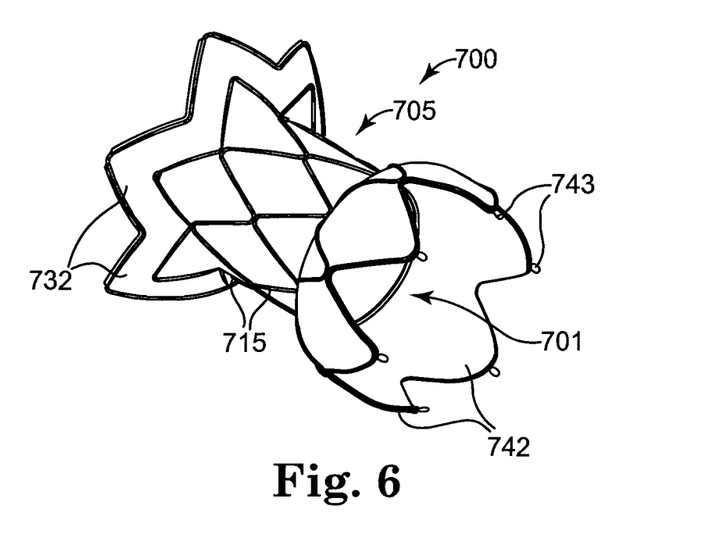
FIG. 6 is a perspective view of an infundibular device, in accordance with the present invention.
Figure 7:
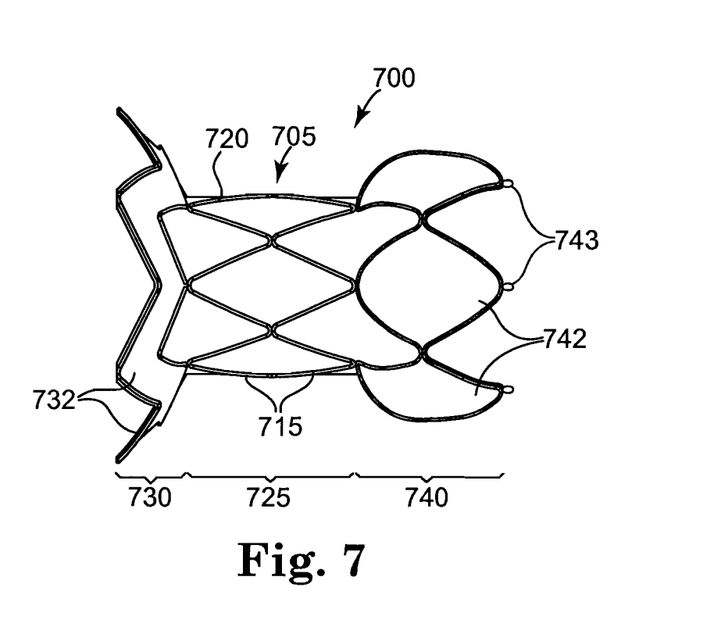
FIG. 7 is a side view of the infundibular device of FIG. 6.
Figure 8:
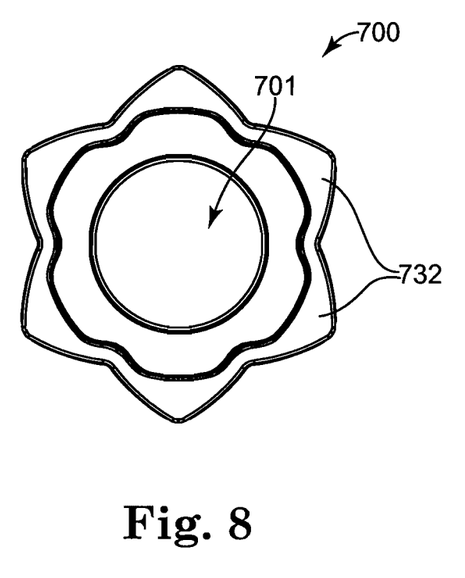
FIG. 8 is an end view of the infundibular device of FIGS. 6 and 7.

Another preferred embodiment of the present invention is device 700 shown in FIGS. 6-8. Device 700 includes a stent portion 705 with a middle portion 725 and two end portions 730, 740. As shown, the end portions 730, 740 are different in device 700. End portion 730 has a larger diameter, and the wires 715 in the end portion 730 are in a nested configuration. End portion 740, on the other hand, is smaller in diameter than end portion 730 and the wires 715 are in a point-to-point configuration. Device 700 may be arranged in an implantation site such that end portion 730 or end portion 740 is located more distal, or vice versa. Device 700 also illustrates that a plurality of different configurations of devices are contemplated by the present invention.

The prosthetic valve or infundibular reducer device of the present invention may be part of a delivery system. One exemplary such delivery system is described in co-pending non-provisional patent application Ser. No. 12/358,388 titled "Infundibular Reducer Device Delivery System and Related Methods," filed on Jan. 23, 2009, and incorporated herein by reference in its entirety. The infundibular reducer devices of the present invention may be fastened to such a delivery system using a fastening means. A plurality of loops 133 provided on or near the proximal end (for example, on the crowns of at least one of the end portions) of the infundibular reducer device is one example of such a fastening means. Such loops 133 may be formed from, for example, sutures or from the fabric used to form part of the stent 105. Preferably, the attachment loops 133 resemble belt loops, and do not maintain a significant profile so as to not impede blood flow. Other fastening means besides loops 133 are also contemplated by the present invention.

Below is a description of additional or optional features that can be included with any of the infundibular reducer devices described above and or other stent-based devices that can be used in the same or different parts of the body.

Another feature that can be included in the device of the present invention is to include silver in the stent portion. Silver can be applied to or included in the stent portion in various ways. For example, silver may be applied by using thread impregnated with silver in the stent portion. The silver thread could be applied near where a replacement valve is attached to the stent portion. The silver thread could help prevent excessive tissue ingrowth, which could negatively affect the function of the valve. Distance between the valve portion and a concentration of silver would depend upon a margin of inhibition necessary as well as a duration needed as the device is accepted by the body. It is likely that full ingrowth would be desired for areas contacting the patient's anatomy, but inhibition of growth could be desired. The silver may also be used as an antimicrobial agent, which helps prevent infection. Thus, a stent portion of a device of the present invention can include such silver impregnated thread in locations where infections are likely to develop.

Another purpose for using silver thread is that silver may be viewed under fluoroscopy. Thus, the silver may act as a marker when seeking to locate the valve under fluoroscopy for monitoring and/or subsequent location for deployment or during other procedures.

Yet another possible feature of the device of the present invention is inclusion of a pattern of radiopaque markers. An example may be including a radiopaque marker or markers in the shape or pattern of a ring located circumferentially around the ends of the valve portion of the device. Such a ring could be applied directly, with ink, or thread, or tape or other means. In particular, such a ring could allow for easy identification and location of the valve portion of the device of the present invention under fluoroscopy for monitoring and/or subsequent deployment procedures. It is also possible to have a plurality of bands or radiopaque material generally equally spaced along the length of the valve portion. The purpose of the markers would be to locate the valve, especially during subsequent deployment of future prosthetic valves. Another possibility would be to add radiopaque thread markers on the stent portion at various locations. One particular material that can be used as a radiopaque marker is a platinum strand or cable.

Yet another possible feature of the device of the present invention is to embed materials into the fabric used in the stent portion. These materials can be used to enhance tissue ingrowth. The purpose of tissue ingrowth is to secure the device as well as help close any paravalvular leaks. Some exemplary materials that can be embedded include, but are not limited to, collagen, hydrophilic materials, gelatins, albumen, or other proteins. The material could be put into solution and the fabric of the stent portion could be soaked in the solution. The stent portion could then be stored in saline and post-sterilized to prevent destruction of the material in glutaraldehyde or other storage chemical sterilant.

A further possible feature of the device of the present invention is the addition of a felt edge on the device. The felt edge would preferably be located on the crowns of at least one of the two end portions. The purpose of adding felt to the edge is to control tissue ingrowth and thrombosis. The felt can facilitate rapid ingrowth of tissue due to its porous nature. Other areas of the stent may be made of a knit or weave where the maximum amount of ingrowth is not necessarily desired. Rapid, healthy tissue ingrowth on the edges of the stent portion, where the stent portion contacts the body, will aid in fixation of the stent to help prevent migration as well as provide strain relief from the remainder to the stent and vessel.

Further embodiments of the present invention are possible by varying the permeability or porosity of the fabric used in the device. A semi-permeable material may, for example, be desired to enhance tissue ingrowth of the endothelium into the device. In other cases, the fabric may not be desired to be permeable. It is contemplated that all levels of permeability and porosity are possible for the fabric material of the devices of the present invention.

Another possible feature of the present inventive device is adding a hydrophobic material to the stent portion. A hydrophobic material, such as Ultra High Molecular Weight Polyethylene (UHMWPE), polypropylene, etc. could be applied in a variety of ways including using thread made entirely or in part from one of these hydrophobic materials. The material would not need to be applied to all thread, however. For example, hydrophobic thread could be applied at the margin of the implanted valve portion to help prevent excessive tissue ingrowth which could affect the function of the valve. The distance from the valve and the concentration of material would depend upon the margin of inhibition necessary as well as the duration needed as the device is accepted by the body. It is likely that full ingrowth would be desired for the areas contacting the patient anatomy and inhibition of growth within the valve portion. The purpose of using a hydrophobic material may include reducing tissue ingrowth as well as reducing thrombosis.

Another optional feature of the present invention can be seen in the embodiment shown in FIG. 4. The wires 415 in the end portions 430 can be seen to have a point to point configuration of the bends. The purpose of such a configuration is to keep excess fabric from being in the path of blood flow through the device 400. Particularly, this configuration is desired at the in-flow end of the device 400.

A further optional feature of the present invention is to add a weave or braid of structural thread to the stent portion in the area where it contacts the valve portion. The angle of the braid or weave is based upon providing a firm fit for the valve portion in the stent portion, but allows for expansion at the rate of subsequent valved stents.

In some embodiments, the stent of the present invention may be completely self-expanding based upon the choice of materials and configuration of the wires. In other embodiments, the stent may be moderately self-expanding and may use a balloon to assure complete expansion. In such an embodiment, the wires may comprise MP35N, for example. For example, it may be desired to have the end portions of the device self-expandable while the middle portion, including the valve, is balloon-expandable.

It is contemplated that the device of the present invention may not be removed once the replacement valve portion of the device no longer functions, such as after a significant period of time has passed since implantation. The device may then serve as a landing zone or location where a replacement valve may be implanted or docked. One exemplary valve that may be implanted within the present inventive device is the Melody™ Transcatheter Pulmonary Valve, made by Medtronic, Inc., Minneapolis, Minn., U.S.A., which is a bovine jugular vein valve. It is contemplated, however, that other similar devices may also be implanted within the present inventive device. The device of the present invention preferably includes a stent portion that is able to expand to surround the replacement device.

The present invention has now been described with reference to several embodiments thereof. The entire disclosure of any patents, patent applications, publications and journal articles identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A prosthetic valve assembly comprising:
a radially self-expandable stent configured to expand to bear against a wall of a native body lumen, the stent comprising:
a central portion comprising a plurality of wires and a diameter, and being compressible and expandable along its entire length, at least some of the plurality of wires of the central portion being arranged in a point-to-point configuration;
a first end portion adjacent a first end of the central portion, the first end portion including a first wire extending along an entire first circumference of the first end portion; and
a second end portion adjacent a second end of the central portion, the second end portion including a second wire extending along an entire second circumference of the second end portion,
wherein each of the first and second wires are longitudinally spaced along theft entire length by a gap distance from the wires of the central portion;
an implantable prosthetic valve, having a diameter, the valve being mounted inside the central portion of the stent; and
a fabric,
wherein a diameter of at least a portion of each of the first and second end portions of the stent is greater than the diameter of the central portion, and
wherein the first and second end portions and the central portion are attached to the fabric.

2. The prosthetic valve assembly of claim 1, wherein each of the first and second end portions comprises a plurality of wires that are in a nested configuration relative to each other.

3. The prosthetic valve assembly of claim 1, wherein the plurality of wires of the central portion, first end portion, and second end portion comprise a material having shape memory.

4. The prosthetic valve assembly of claim 1, wherein the plurality of wires of the central portion, first end portion, and second end portion comprise a plurality of different materials.

5. The prosthetic valve assembly of claim 2, wherein the plurality of wires of the central portion, first end portion, and second end portion are circular in shape and include a plurality of sinusoidal bends.

6. The prosthetic valve assembly of dam 5, wherein the sinusoidal bends in the wires have different sizes.

7. The prosthetic valve assembly of claim 2, wherein at least some of the plurality of wires are in a point-to-point configuration.

8. The prosthetic valve assembly of claim 1, wherein each of the first and second end portions comprises a gap around its entire circumference between two adjacent wires.

9. The prosthetic valve assembly of claim 1, wherein the end portions have tapered diameters in directions toward the central portion.

10. The prosthetic valve assembly of claim 9, wherein the central portion is cylindrical in shape.

11. The prosthetic valve assembly of claim 1, wherein the fabric is a knit fabric.

12. The prosthetic valve assembly of claim 8, wherein the central portion and each end portion are articulable with respect to each other.

13. A prosthetic valve assembly comprising:
a radially self-expandable stent comprising a middle portion being compressible and expandable along its entire length and having a smaller diameter than end portions thereof, with the end portions configured to expand to bear against a wall of a native body lumen;
an implantable prosthetic valve mounted inside the middle portion of the stent; and
a fabric,
wherein the middle portion comprises a plurality of circumferential wires arranged in a point-to-point configuration relative to each other, and wherein the end portions each comprise at least one circumferential wire extending along an entire circumference of the respective end portion, each wire being longitudinally spaced along its entire length from the wires of the middle portion,
wherein the middle portion and the end portions are attached to the fabric.

14. The prosthetic valve assembly of claim 13, wherein the wires of the middle and end portions comprise a plurality of different materials.

15. The prosthetic valve assembly of claim 13, wherein the wires of the middle and end portions are circular in shape and include a plurality of bends.

16. The prosthetic valve assembly of claim 15, wherein the bends in the wires are sinusoidal in shape.

17. The prosthetic valve assembly of claim 13, wherein the wires of the middle and end portions comprise a material having shape memory.

18. The prosthetic valve assembly of claim 13, wherein the end portions have tapered diameters in directions toward the middle portion.

19. The prosthetic valve assembly of claim 13, wherein the middle portion is cylindrical in shape.

20. The prosthetic valve assembly of claim 13, wherein the fabric is a knit fabric.

21. The prosthetic valve assembly of claim 13, wherein the middle portion and each end portion are articulable with respect to each other.

22. The prosthetic valve assembly of claim 13, wherein at least some of the plurality of wires are in a nested configuration.

* * * * *

UNITED STATES PATENT AND TRADEMARK OFFICE
CERTIFICATE OF CORRECTION

PATENT NO.        : 8,801,776 B2                                      Page 1 of 1
APPLICATION NO.   : 12/391330
DATED             : August 12, 2014
INVENTOR(S)       : House et al.

It is certified that error appears in the above-identified patent and that said Letters Patent is hereby corrected as shown below:

In the Claims

In Claim 1, column 13, lines 30,31
"... longitudinally spaced along theft entire ..." should read -- "... longitudinally spaced along their entire ..." --

In Claim 6, column 13, line 56
"... valve assembly of dam 5, wherein the ..." should read -- "... valve assembly of claim 5, wherein the ..." --

Signed and Sealed this
Seventh Day of July, 2015

Michelle K. Lee
*Director of the United States Patent and Trademark Office*